United States Patent [19]
Dory

[11] Patent Number: 5,150,711
[45] Date of Patent: Sep. 29, 1992

[54] ULTRA-HIGH-SPEED EXTRACORPOREAL ULTRASOUND HYPERTHERMIA TREATMENT DEVICE

[75] Inventor: Jacques Dory, Coupvray, France

[73] Assignee: EDAP International, S.A., France

[21] Appl. No.: 734,667

[22] Filed: Jul. 23, 1991

Related U.S. Application Data

[60] Continuation-in-part of Ser. No. 696,992, May 3, 1991, which is a continuation of Ser. No. 427,429, Oct. 27, 1989, Pat. No. 5,054,255, which is a continuation-in-part of Ser. No. 368,906, Jun. 19, 1989, Pat. No. 5,080,101, which is a continuation of Ser. No. 37,369, Apr. 13, 1987, abandoned, which is a division of Ser. No. 728,905, Apr. 30, 1985, Pat. No. 4,658,828, which is a continuation-in-part of Ser. No. 674,889, Nov. 26, 1984, Pat. No. 4,617,931.

[30] Foreign Application Priority Data

Jul. 23, 1990 [FR] France ............................ 90 09717

[51] Int. Cl.$^5$ ............................................. A61B 8/00
[52] U.S. Cl. ............................... 128/660.03; 128/399
[58] Field of Search ............. 128/660.03, 24 AA, 399, 128/804, 660.09, 660.10

[56] References Cited

U.S. PATENT DOCUMENTS

| | | | |
|---|---|---|---|
| 4,620,546 | 11/1986 | Aida et al. | 128/24 AA |
| 4,875,487 | 10/1989 | Seppi | 128/399 |
| 4,936,303 | 6/1990 | Detwiler et al. | 128/399 |
| 5,005,580 | 4/1991 | Okazaki | 128/660.03 |
| 5,036,855 | 8/1991 | Fry et al. | 128/660.03 |
| 5,080,102 | 1/1992 | Dory | 128/660.03 |

*Primary Examiner*—Francis Jaworski
*Assistant Examiner*—George Manuel
*Attorney, Agent, or Firm*—William A. Drucker

[57] ABSTRACT

An extracorporeal ultra-high-speed ultrasound hyperthermia treatment device adapted to enable focussed emission of ultrasound wave trains at frequencies between 0.5 and 10 MHz with peak powers between 10 kW and a few hundred watts, the parameters which define the concentration of the treatment beam in the focal spot and the power being determined so that, irrespective of the depth and the nature of the tissue, the treatment time is in the order of that enabling significant destruction, preferably total destruction, of the target during the linear part of a curve showing the temperature increase as a function of time.

8 Claims, 3 Drawing Sheets

ULTRA-HIGH-SPEED EXTRACORPOREAL ULTRASOUND HYPERTHERMIA TREATMENT DEVICE

"CROSS REFERENCE TO PRIOR APPLICATIONS

This application is a continuation-in-part of Ser. No. 07/696,992, filed May 3, 1991, which is a continuation of Ser. No. 07/427,429, filed Oct. 27, 1989, now U.S. Pat. No. 5,054,255, which is a continuation-in-part of Ser. No. 07/368,906, filed Jun. 19, 1989, U.S. Pat. No. 5,080,101, which is a continuation of Ser. No. 07/037,369, filed Apr. 13, 1987, now abandoned, which is a division of Ser. No. 06/728,905, filed Apr. 30, 1985, U.S. Pat. No. 4,658,828, now Reissue No. 33,590, of May 21, 1991, which is a continuation-in-part of Ser. No. 06/674,889, filed Nov. 26,1984, now Re-Examination Certificate B1-4,617,931 of Jul. 12,1988.

BACKGROUND OF THE INVENTION

1. Field of the Invention

The present invention concerns an ultra-high-speed extracorporeal ultrasound hyperthermia treatment device.

2. Description of the Prior Art

It is known, in particular from French patent No 84 06877 filed 3 May 1984 in respect of: "Device for examining and locating tumours by ultrasonic means provided with a device for localized ultrasound hyperthermia treatment", corresponding to my U.S. reissue Pat. No. 33,590 of May 21, 1991 to use a focussed ultrasound beam to cause extremely localized heating of biological tissue in order to destroy tumours.

In the device described in the patent referred to above the beam is emitted in the form of wave trains at a high frequency (0.5 to 5 MHz, for example, the lower frequencies being used to destroy the deeper structures within the body) and with a relatively low peak power (some 10 to 100 watts, the higher powers being used to destroy the deeper structures).

These wave trains are separated by intervals during which it is possible to carry out real time (usually type B) ultrasound scanning to relocate the focus relative to the target (which is affected by natural movements of the tissues caused by breathing) or to examine the damage sustained by the tissues in the treated area.

With the power level and frequencies employed—which depend on the depth of the target area—the target temperature is increased to approximately 45° C., a temperature which is sufficiently high in principle to destroy malignant cells. It has been thought previously that an excessive increase in the temperature of the target area could cause serious burns in the surrounding area as the result of thermal diffusion.

As a result, treatment times are relatively long, possibly several tens of minutes or even several hours.

The invention is based on the discovery that increasing the peak power of the waves used by a factor of 10 to 100, depending on the depth and the absorbing power of the target area, makes it possible, by causing an ultra-high-speed temperature rise, to significantly reduce the effects of thermal diffusion and to destroy the target area in time periods in the order of one second.

SUMMARY OF THE INVENTION

The invention consists in a treatment device of the kind above referred to, which is adapted to enable the focussed emission of ultrasound wave trains at frequencies between 0.5 and 10 MHz with peak powers between 10 kW and a few hundred watts, the parameters which define the whole concentration of the treatment beam in the focal spot and the power being determined so that, irrespective of the depth and the nature of the tissue, the treatment time is in the order of that enabling significant destruction, preferably total destruction, of the target during the linear part of a curve showing the temperature increase as a function of time.

The frequency as well as the diameter of the emitting surface of said device and the diameter of the focal spot are advantageously determined according to the nature and depth of the target so that the concentration of the beam is maximized and the power is then determined for a given value of the frequency and of the selected diameters so that the target is destroyed at a temperature in the vicinity of 58° C., in a time period between 0.5 and 3 seconds.

Tests effected by the applicant have shown that the construction of this device, requiring the implementation of means for quasi-continuous emission at very high peak powers, can minimize the destruction of healthy cells whilst enhancing the effectiveness with which the target is destroyed, in particular as the result of an additional mechanical destructive effect on the cells of the target, so providing a new localized ultrasound hyperthermia treatment technique justifying subsequent use in this description of the term "ultra-high-speed hyperthermia treatment".

Another advantage of ultra-high-speed hyperthermia treatment is that it provides significantly enhanced echographic examination of changes to the target during treatment.

According to another feature of the invention, this examination is carried out by type A or B echography during interruptions in the treatment beam at a given rate such that the echogram or the image has time to undergo detectable modifications (which could mean a few tenths of a second in ultra-high-speed hyperthermia treatment) which are not masked by spurious modifications caused by movement of the wave trains (as is the case in practise with prior art hyperthermia treatment techniques).

The invention also concerns specific type A or B echographic techniques which facilitate the ultra-high-speed detection of change sustained by the target so that treatment can be terminated as soon as the target is destroyed.

Other features and the advantages of the invention will emerge more clearly from the following description in which the ultra-high-speed detection techniques are described first, to facilitate the subsequent description of the construction of the ultra-high-speed hyperthermia treatment device.

DETAILED DESCRIPTION OF THE INVENTION

Figure 1:
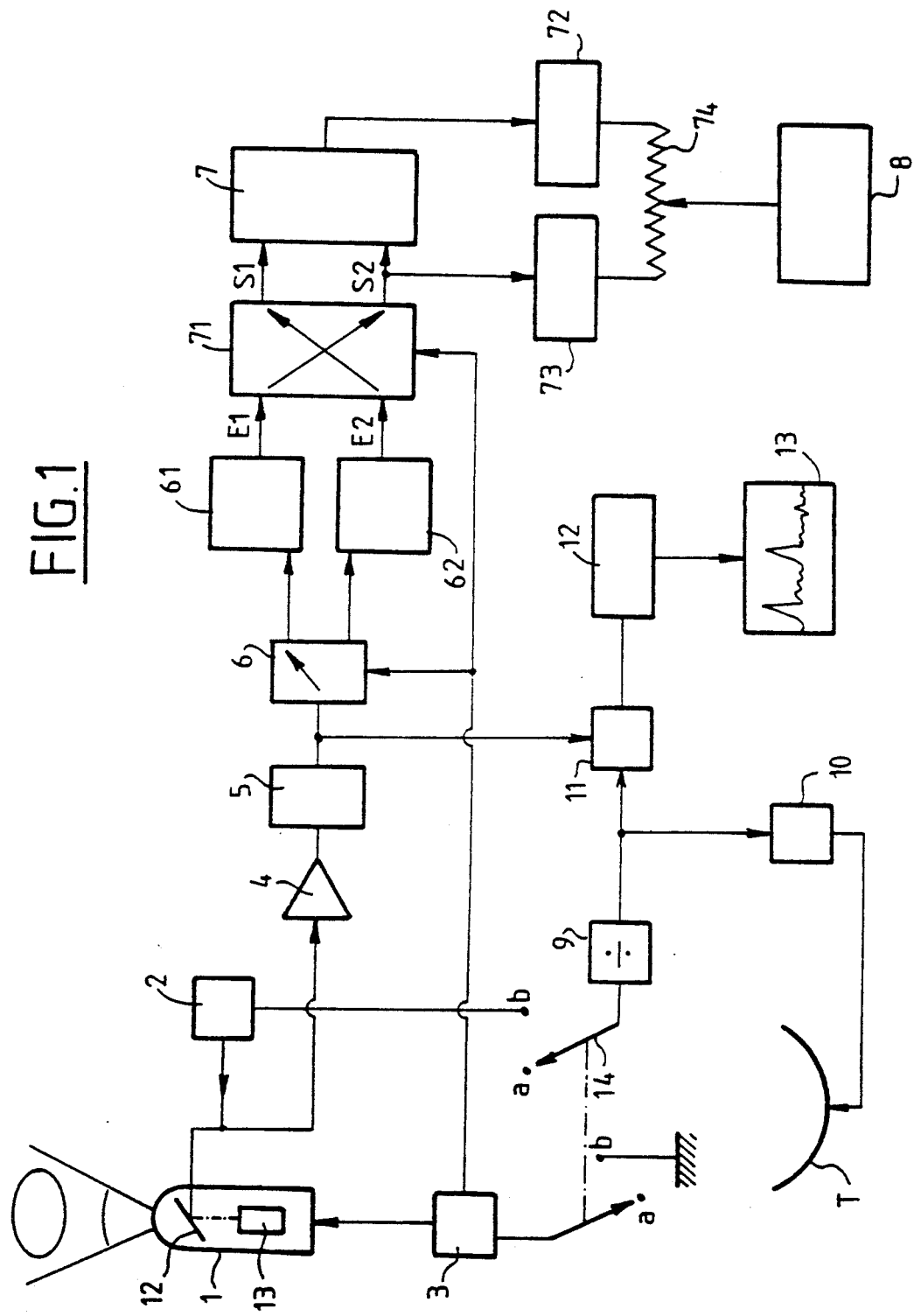
FIG. 1 is a block diagram showing an ultra-high-speed hyperthermia treatment device provided with means for ultra-high-speed detection of change to the target during treatment.

FIG. 1 is a block diagram of a known type echography device comprising a real time probe 1 including a piezo-electric element 12 which is oscillated by an electric motor 13 through a transmission system represented by the chain-dotted line.

For example, this probe may be as described in French patent No 80 16718 filed 29 Jul. 1980 in respect of: "Mechanical sector scanned echographic probe".

Figure 2:
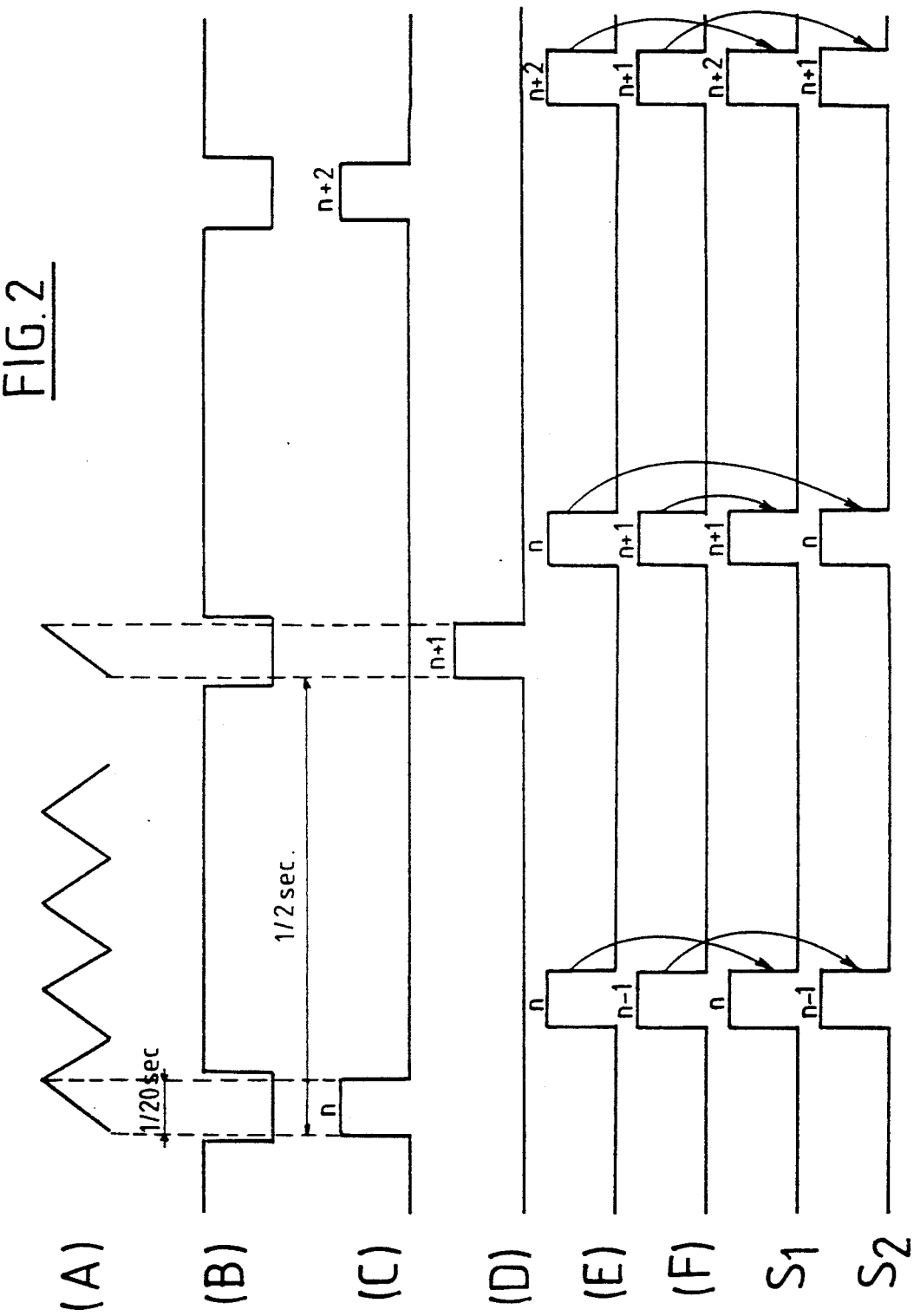
FIG. 2 is a timing diagram showing the operation of said detection means.

The piezo-electric element 12 is excited by a pulse generator 2 and the motor is controlled by a sawtooth scanning signal generator (producing the waveform (A) shown in FIG. 2) to scan a sector of the region to be treated, the scan passing through the focus of the treatment beam emitter.

The pulses reflected from biological structures are amplified by a receiver 4 whose output is connected to an analog-to-digital converter 5.

An electronic switch 6 connects the output of the converter 5 to one or other of two memories 61 and 62. Switching occurs on each scan, the switch 6 being connected to an appropriate output of the sawtooth generator 3 for this purpose.

In each memory addressing of the writing operation is effected in a known manner according to the angular position of the beam emitted by the probe and the time elapsed since the start of each emission, so that a complete image of the treated area is written into one of the two memories on each scan.

The memories are also read in a known way and the resulting signals are fed to a digital subtractor through a switch 71 which reverses the connection between its inputs E1 and E2 and its outputs S1 and S2 on each scan (being connected to the appropriate output of the generator 3 to this end).

If no inversion were applied, the subtractor, which computes the difference between the serial digits which define the successive points of the two images, would subtract the current image from the previous image and then the previous image from the current image, and so on, the inversion being required so that the previous image is always subtracted from the current image in each scan.

The output of the subtractor 7 is connected to a digital-to-analog converter 72 which supplies a voltage for modulating the brightness of the cathode ray tube of a display device 8.

The output S2 is connected to a second digital-to-analog converter 73. A potentiometer 74 provides a variable mix of the output voltage of the converter 72, representing the differential image, and the output voltage of the converter 73, representing the latest image stored.

The operator can then observe either the conventional image of the treated area, enabling a preliminary identification of the structures concerned, or the differential image, enabling him to observe how the structures change during the treatment.

As the treatment uses high peak powers, the images cannot be formed during emission of the treatment beam, the energy of which, reflected from the structures concerned, is sufficient to "dazzle" the echographic transducer. The effect of this can continue for one or more microseconds after the end of emission. It is therefore necessary to emit wave trains separated by gaps (waveform (B) in FIG. 2) slightly longer than the duration of an echographic scan, which might be 1/20 s, for example, and to synchronize the latter with the emission.

It is obviously also necessary for the images to be formed at a sufficiently high rate for natural movement of the tissue as a result of breathing not to introduce excessive differences between two successive images, which would mask the differential effect resulting from the modification of the structures due to the treatment. To give an example, the emission time could be chosen to obtain an image every 0.5 s at least. This implies that the peak power of the treatment emission be sufficient for significant destruction of the target area cells to occur in a few tenths of a second.

FIG. 2 shows at (C) the intervals in which the memory 61 is written, at (D) the intervals in which the memory 62 is written, at (E) the intervals in which the memory 61 is read, at (F) the intervals in which the memory 62 is read and at (G) and (H) the resulting states of the outputs S1 and S2. The numbers of the images in memory are shown. This shows that the previous image is always subtracted from the current image.

Referring again to FIG. 1 the power transducer T, symbolically represented as a spherical cup on which piezo-electric elements are placed, is energized by the treatment beam emitter 10. The transducer is advantageously as described in French patent No 84 06877 and the probe 1, although shown separately, would in practise be attached to the cup, disposed at it center and oriented along its axis, as explained in the aforementioned patent.

FIG. 1 also shows units that are not used in the embodiment of the invention described thus far, but only in the embodiment now to be described.

These units are a variable ratio frequency divider 9, an AND gate 11, a memory 12, a display device 13 and a switch 14.

When the switch 14 is in position a, the divider 9 is connected to the sawtooth generator 3, which is adapted to provide a synchronization signal when the axis of the probe passes through the focus of the treatment beam emitter (the center of the sphere of which the cup T constitutes a portion). The division ratio of the divider is then set to a value between 1 and 5, for example.

It therefore provides every N scans a short signal applied to the power emitter 10 which disables it for its duration of approximately 1 ms.

The short signal is also applied to the gate 11 which is therefore enabled for 1/1 000 s and passes to the memory 12 the digital signal from the converter 5.

The memory 12 has the time to acquire information representing a scanning line, the duration of which is in the order of only 0.2 ms (as compared with 0.2 to 0.02 s to acquire a complete image).

Thus in this embodiment the treatment beam will be interrupted for one 1 ms during the duration of the treatment beam pulses, and this will occur every 1/20 s, for example, resulting in only a very slight reduction (2%, for example) of the mean power as compared with an uninterrupted treatment beam.

The line acquired "on the fly" in this way, every 1 to 5 scans, passes through the focus. This application uses type A ultrasound scanning and the information collected in one direction only is sufficient. An equivalent result could be obtained by immobilizing the probe in a particular direction through the target.

The echo signals stored in the memory 12 are read out at a rate of 50 Hz, for example, and displayed continuously on the screen of the device 13.

This reading frequency promotes visual comfort.

The eye of the operator performs the equivalent of the digital subtraction of the information collected during treatment, at a rate such that it can perceive changes in the amplitude of the ultrasound scan.

It should be understood that using a type B ultrasound probe to obtain type A echograms has the advantage of enabling the same probe to be used for type B ultrasound scanning before a target is treated (here the term "target" refers to a part of the tumour which is exactly the same size as the focal spot, and complete treatment of the tumour will entail focussing the beam onto the various target areas constituting it in succession), to locate said target area as described in the previously mentioned French patent No 84 06877. A relocation can even be carried out by the same probe for type B ultrasound scanning during the treatment of a target, by interrupting the treatment beam for a sufficient time to obtain an image (1/20 s).

Figure 3:
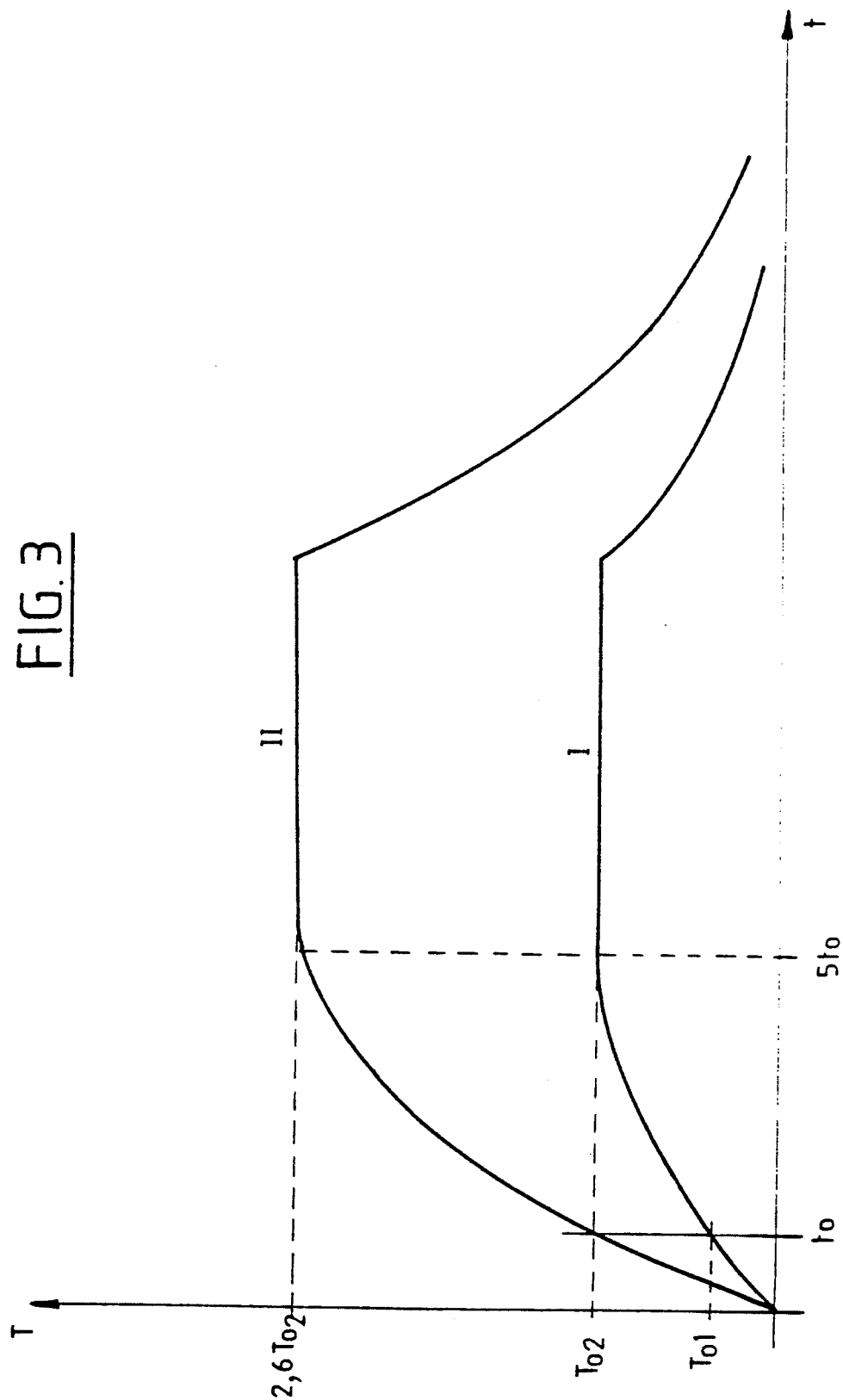
FIG. 3 shows curves representing the temperature increase of a biological tissue as a function of time.

The other features of the ultra-high-speed hyperthermia treatment device will now be explained with reference to FIG. 3.

This shows, for a small heat source (in this example a small diameter focal spot), the experimentally determined increase in the temperature T of the area acted on by an ultrasound beam as a function of the application time, for two different applied power levels (curves I and II).

The temperature rise is seen to be linear over a time to which is substantially the same for both curves but corresponds to different temperatures, respectively $T_{o1}$ and $T_{o2}$. The slope of the curves then decreases to a ceiling after equal time periods of $5 \times t_o$. The ceiling temperature is approximately $3 \times T_{o1}$ for the first curve and $2.6 \times T_{o2}$ for the second.

Note that $t_o$ is independent of the applied power and is in direct proportion to the focal spot diameter. In the experiments yielding the curves shown in FIG. 3, $t_o = 0.5$ s.

In a preferred embodiment of the invention, the device is adapted so that total destruction of the cells is obtained after a time of $t_o$ at most.

It has been found by the applicant that this produces minimal damage to tissues in the area surrounding the target.

This experimental result can be explained by the fact that, in the linear region of the curve, losses by diffusion are negligible in comparison with the heat input. Beyond this point the losses are proportional to the temperature gradient between the target and the surrounding tissue, and so increase rapidly until they are equal to the heat input (at the ceiling temperature). When the input of heat is terminated, the temperature of the target decreases exponentially to a value at which there is substantially no more destruction after a time in the order of 3 to $6 \times t_o$ in these experiments. This time (in the order of 1.5 to 3 s in this case) will substantially define the preferred gap between two successive wave trains of the treatment wave, so that all wave trains are subject to minimal losses by diffusion.

In FIG. 2, where the wave train duration is slightly less than 0.5 s, a value chosen because it corresponds $t_o$, the successive wave trains, separated by only 0.05 s, will be applied to different targets in the tumour, a single wave train being sufficient to compare the reflective state of each target before and after it is applied.

It is known that the time t to destroy tumour cells is proportional to the temperature T to which they are subjected from a threshold value $T_i$ of the latter which is 43° C., for example. For T = 58° C., the value of t is in the order of 0.5 s, so that the device will be set up to achieve a temperature of 58° C. in the target. The application time t is substantially halved for each increase in temperature of 1° C. above 43° C., so that it is divided by 1 000 on increasing from 50° to 60° C., for example.

To raise the target temperature approximately 20° C. above normal in 0.5 s, representing a rate of temperature increase of 40° C./s, the following parameters apply: firstly, the focal length is determined by the depth of the target. The device is set up to provide three values of the focal length, namely: 4 to 15 cm (for destroying deep tumours), 3 to 4 cm (tumours at intermediate depths) and 1 to 1.5 cm (treatment of the eye, for example).

The operating frequency is determined for each focal length so that the concentration of ultrasound energy on the focal spot is maximized.

Experience shows that when this first condition is met, for a given emission power, the risk of damaging surrounding tissue is minimized while the energy density at the focal spot is maximized.

A possible explanation for this is that the concentration is the product kg/ka, where ka is an attenuation factor which increases in direct proportion to the frequency (experience shows that the attenuation is in the order of 1° C. per cm of path and per MHz) and kg is equal to $(Do/do)^2$, where Do and do are the respective diameters of the emitting surface and the focal spot.

The geometrical concentration factor kg represents the ratio of the intensities that would be obtained at the source and at the focal spot in the absence of any attenuation on the path of the beam, and it is therefore the factor ka which must be minimized to avoid losses of energy in the tissues passed through, which account for only a small percentage of the energy absorbed by the tissues, which is the only part converted into heat.

The concentration, the residual energy in the focal spot and the rate of temperature increase at the target have been calculated by the applicant as a function of the focal length, the entry diameter of the beam into the tissue and the frequency for a constant aperture angle of the beam and an emitted power of 1 kW.

These calculations show that the residual energy is in inverse proportion to the frequency, but that the maximum residual energy does not reflect the maximum concentration and therefore the fastest temperature increase.

This may be explained by the fact that the frequency affects ka and the rate of temperature increase in the opposite sense to its effect on kg.

For example, for an emitted power of 1 kW, respective focal lengths of 10 and 12 cm and respective tissue entry diameters of 10 and 12 cm, the optimum frequency determined in this way is 1 MHz yielding temperature increase rates of 33.97° C./s and 21.43° C./s, respectively. The power should therefore in theory be equal to 1.2 and 1.9 kW, respectively, to achieve the required rate of temperature increase of 40° C./s. As a safety measure, a power significantly higher than these values (10 kW, for example) is used, to allow for the fact that the temperature of 58° C. will not be reached until the end of each pulse of the treatment beam.

Other things being equal, for focal lengths of 3 and 5 cm and respective entry diameters of 3 and 5 cm, the respective optimal frequencies will be 3 and 1.5 MHz and the respective rates of temperature increase will be 384.89° C./s and 135.91° C./s. The thermal power theoretically required will then be substantially less than 1 kW. Powers of between 2 and 5 kW will be used as a precautionary measure, however.

For a focal length of 1.5 cm the optimum frequency will be 6 MHz and the temperature increase 1 539.57° C., requiring in practise a power level in the order of several hundred watts.

Generally speaking, the peak powers used in ultra-high-speed hyperthermia treatment, especially to treat deep tumours, require that special provisions are embodied in the construction of the device. In particular, it is necessary to use piezo-electric ceramic materials capable of supporting such high peak powers and of cooling quickly. Forced cooling arrangements may be needed. The supply of power to the electrical generator may require the use of auxiliary power supplies.

Note that the optimum power values specified should not be significantly exceeded, to avoid the risk of lesions affecting the surrounding tissue. It has been shown that the diameter of the area within which the temperature rise resulting from the diffusion of heat energy accumulated in the focal region at the moment when application of power is terminated remains sufficiently high to destroy the cells relatively quickly increases in proportion to the square root of the temperature increase in the focal region, which increase is in turn proportional to the power.

Finally, note that at the powers indicated the ultrasound beam is progressively transformed to a significant degree during its propagation, the result being the appearance of components at higher frequencies than those of the original beam.

These high frequency components are more strongly absorbed by the tissue and therefore have a greater thermal effect.

The frequencies and powers chosen enable the beam to pass with little damage through the outer layers of tissue and to produce a thermal effect at the focal spot.

The beam additionally has a mechanical effect which complements its thermal effect for increased treatment efficacy.

There is claimed:

1. In an extracorporeal ultrasound hyperthermia target treatment device comprising:
   a) means generating a treatment beam from an emitting surface; and means locating a treatment beam target in a body;
   b) means aiming and focusing said beam at said target at a focal spot; the improvement comprising:
   c) in said treatment beam generating means means for producing ultrasound wave trains at frequencies between about 1 MHz and about 6 MHz, as a function of frequency; and peak electric powers between about 10 KW and 1 KW, as a function of frequency; and peak acoustic powers between about 3 KW and 200 watts, as a function of frequency; which produce acoustic intensity at the focal spot between about 100 KW and 10 KW per square centimeter, as a function of frequency, for less than about three seconds.

2. Device according to claim 1 further comprising means for determining the diameter of the emitting surface of said device and the diameter the focal spot are so that the concentration of the whole treatment beam is maximized and the power is is a function of a given value of the frequencies and the diameters determined so that the target is destroyed at a temperature in the vicinity of 58° C. in a time period between 0.5 and 3 s.

3. Device according to claim 1 wherein the wave trains are separated by periods in the order of 1.5 to 3 s.

4. Device according to claim 1 wherein an emission power on the order of 10 KW corresponds to focal lengths of 10 and 12 cm and a frequency of 1 MHz, an emission power of between 2 and 5 kW corresponds to focal lengths of 3 and 5 cm and frequencies of 3 and 1.5 MHz, respectively, and an emission power on the order of a few hundred watts corresponds to a focal length of 1.5 cm and a frequency of 6 MHz.

5. Device according to claim 1 comprising means for echographic examination of damage to the target during treatment, said examination means executing type B echography of the target and further comprising means to compare two consecutive images taken before and after at least one treatment wave train.

6. Device according to claim 5 comprising display means for storing successive images formed by echographic examination in the form of digital information and for forming differential image by subtracting the stored information point by point.

7. Device according to claim 6 comprising display means for superposing a stored image on the differential image.

8. Device according to claim 1 comprising type A echography means for examining damage to the target during treatment from a type B echography probe to capture echoes at the time the examination beam passes through a predetermined direction and during interruptions of the treatment beam.

* * * * *